US008747481B2

(12) United States Patent
Maurer (10) Patent No.: US 8,747,481 B2
(45) Date of Patent: Jun. 10, 2014

(54) REVERSE JOINT REPLACEMENT DEVICE AND METHODS THEREOF

(76) Inventor: Brian Ted Maurer, Morton, IL (US)

( * ) Notice: Subject to any disclaimer, the term of this patent is extended or adjusted under 35 U.S.C. 154(b) by 0 days.

(21) Appl. No.: 13/448,906

(22) Filed: Apr. 17, 2012

(65) Prior Publication Data

US 2012/0271425 A1    Oct. 25, 2012

Related U.S. Application Data

(60) Provisional application No. 61/477,710, filed on Apr. 21, 2011.

(51) Int. Cl.
*A61F 2/32* (2006.01)
(52) U.S. Cl.
USPC ...................................... 623/22.11; 623/22.15
(58) Field of Classification Search
CPC ..................................... A61F 2/40; A61F 2/34
USPC ...................... 623/19.11–19.14, 22.11, 22.15, 623/22.4–22.46
See application file for complete search history.

(56) References Cited

U.S. PATENT DOCUMENTS

| 3,916,451 A * | 11/1975 | Buechel et al. ............... 623/23.4 |
| 2007/0156246 A1* | 7/2007 | Meswania et al. .......... 623/19.12 |
| 2007/0173945 A1* | 7/2007 | Wiley et al. ................. 623/19.13 |
| 2011/0218637 A1* | 9/2011 | Termanini ................... 623/22.15 |

FOREIGN PATENT DOCUMENTS

WO    WO/2011/112353 A1    9/2011

* cited by examiner

*Primary Examiner* — Jason-Dennis Stewart
(74) *Attorney, Agent, or Firm* — Billion & Armitage; Benjamin C. Armitage (57) ABSTRACT

Embodiments relate to a joint replacement device, including a fixed socket including an inner surface and an outer surface supporting a ball, an articulating socket including an inner surface and an outer surface the inner surface in contact with the ball and a stem component attached to the outer surface of the articulating socket. The inner surface of the articulating socket articulates with the ball and the outer surface of the articulating socket can articulate with the inner surface of the fixed socket.

19 Claims, 7 Drawing Sheets

REVERSE JOINT REPLACEMENT DEVICE AND METHODS THEREOF

CROSS REFERENCE TO RELATED APPLICATIONS

This is a non-provisional patent application claiming priority under 35 USC §119(e) to U.S. Provisional Patent Application Number 61/477,710 filed on Apr. 21, 2011, which is incorporated by reference in its entirety.

BACKGROUND

Traditionally, the socket portion of a standard total hip replacement consists of a metal hemispheric socket with a porous outer surface to facilitate bone growth into the socket. The socket also includes a liner on the inner surface for articulation with the ball. The femoral side of a hip replacement usually includes a ball supported by a stem component forced into the center, hollow portion of the bone of a patient. The stem is fastened to the femur with either cement or by bone growth into a porous outer surface of the stem. The ball, positioned on the end of the stem, articulates with the liner of the socket and is attached to the stem via a cold weld and trunnion.

A common problem in hip replacements is dislocation. In dislocation, the ball (which is held in the socket by soft tissue around the hip) comes out of the socket causing great pain and the inability to use the hip or walk. The ball must be manipulated back into the socket with sedation or even general anesthesia. The sedation or anesthetic carries risk, as does the manipulation of the hip-components can break or come loose during the manipulation. Once a hip has dislocated, it is more likely to re-dislocate and may happen enough to require repeat surgery. Revision surgery for hip dislocation is often unsuccessful or not worth the risks to the patient.

The most common method of hip dislocation is for the ball to fall out of the bottom of the socket when the hip is flexed, adducted or internally rotated. This dislocation occurs because the ball moves beyond the coverage of the socket with this maneuver and thus slips out of place. Once out of place, it usually stays there and is accompanied by significant spasms and pain.

SUMMARY

Embodiments relate to a joint replacement device, including a fixed socket including an inner surface and an outer surface supporting a ball, an articulating socket including an inner surface and an outer surface the inner surface in contact with the ball and a stem component attached to the outer surface of the articulating socket. The inner surface of the articulating socket articulates with the ball and the outer surface of the articulating socket can articulate with the inner surface of the fixed socket.

Embodiments also relate to a reverse joint replacement socket including a substantially hemispherical socket and a ball attached to an inner surface of the socket. The socket can attach to an acetabulum or glenoid fossa. Additionally, embodiments describe a reverse joint replacement device including an articulating socket including an inner surface and an outer surface the inner surface in contact with a ball and a stem component, attached to the outer surface of the articulating socket. The inner surface of the articulating socket articulates with the ball and the outer surface of the articulating socket can articulate with an inner surface of a fixed socket.

Embodiments also relate to methods thereof.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail in order to avoid unnecessarily obscuring the invention. The drawings show, by way of illustration, specific embodiments in which the invention may be practiced. These embodiments may be combined, other elements may be utilized or structural or logical changes may be made without departing from the scope of the invention. Accordingly, the specification and drawings are to be regarded in an illustrative, rather than a restrictive, sense.

All publications, patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more". In this document, the term "or" is used to refer to a nonexclusive or, such that "A, B or C" includes "A only", "B only", "C only", "A and B", "B and C", "A and C", and "A, B and C", unless otherwise indicated. The terms "above" and "below" are used to describe two different directions in relation to the center of a composite and the terms "upper" and "lower" may be used to describe two different surfaces of a composite. In the appended aspects or claims, the terms "first", "second" and "third", etc. are used merely as labels, and are not intended to impose numerical requirements on their objects.

Embodiments of the present invention describe a reverse joint replacement device and methods thereof. Although described often as useable in a hip replacement surgery, the device may also be used for shoulder replacement surgeries. In the reverse joint replacement device, the fixed socket is still placed in the patient's own socket or acetebulum (or glenoid fossa for shoulder surgeries), but a liner is not required, in the traditional manner, on the inner surface of this socket. Instead, a ball is attached to the inner surface of the fixed socket. An articulating socket is then attached to the stem component and articulates with the ball.

With the ball and socket reversed, the hip becomes more stable as it undergoes flexing, adducting or internal rotation. Dislocation is now much less likely to occur, if not completely prevented. If the device starts to dislocate, it will be stopped by the fixed socket. The fixed socket may be lined on its periphery to articulate with the outer surface of the articulating socket, if the articulating socket dislocates from the ball. This mechanism provides an additional layer of prevention from dislocation. The articulating socket articulates with the ball in a more stable fashion and the outer surface of the socket can itself articulate with the inner surface of the fixed socket, if necessary to prevent dislocation.

This reverse joint replacement device and method may be utilized in a primary surgery or in a revision surgery. Frequently, in revision surgery, the socket must be removed which increases the magnitude of the surgery tremendously. This is not desirable, as the most common dislocation patients are elderly women who often suffer complications from major surgeries. In a revision surgery, the ball may be attached to the existing fixed socket, such as by utilizing the insertion tool fitting of the fixed socket used to originally place the socket in the primary surgery. The articulating socket can then replace the existing ball on the stem component, without removing it from the patient's bone. Revising the articulating surfaces requires significantly less surgery than revising whole implants at their bone or metal interfaces—whether cemented or bone ingrown porous.

Figure 1:
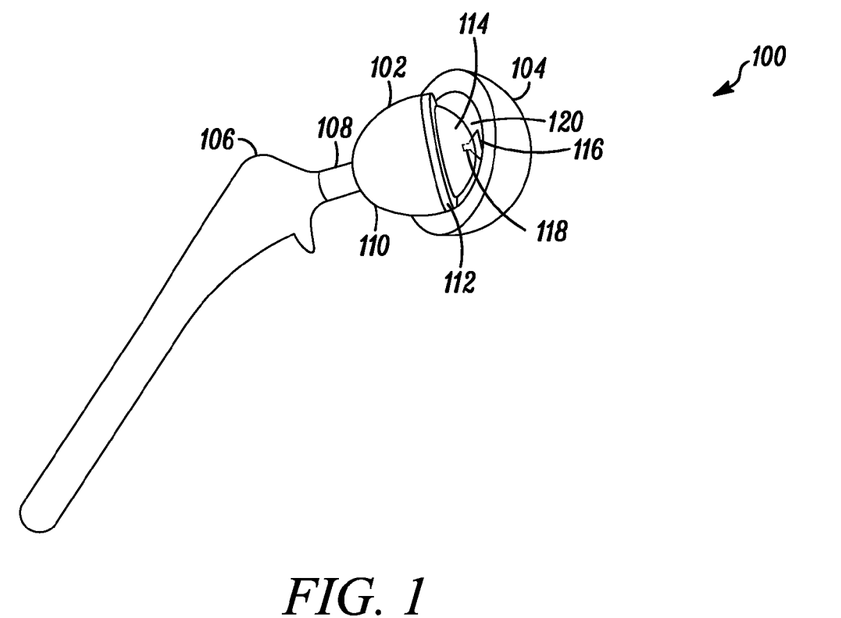
FIG. 1 is a perspective view of a reverse joint replacement device, according to some embodiments.

Referring to FIG. 1, a perspective view 100 of a reverse joint replacement device is shown, according to some embodiments. A stem component 106 is in contact with an articulating socket 102. The stem component 106 and articulating socket 102 may be one-piece construction or be in contact via a fitting. An example of a fitting includes male trunnion 108 and female trunnion 110. The articulating socket 102 may optionally include a liner or lining 112.

Figure 2:
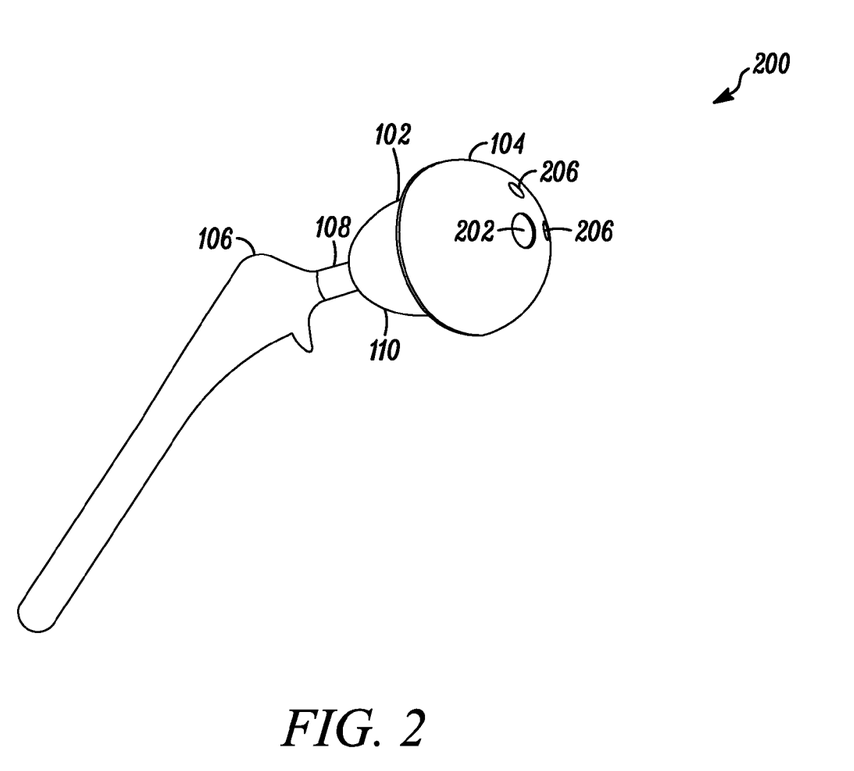
FIG. 2 is a prospective view of a reverse joint replacement device, according to some embodiments.

A fixed socket 104 supports a ball 114 on the inner surface 120 of the fixed socket 104. The ball 114 may be one-piece construction with the socket 104 or attached via a post 118 with base 116, for example. The articulating socket 102 contacts and articulates with the ball 114 (see view 200 of FIG. 2).

Figure 4:
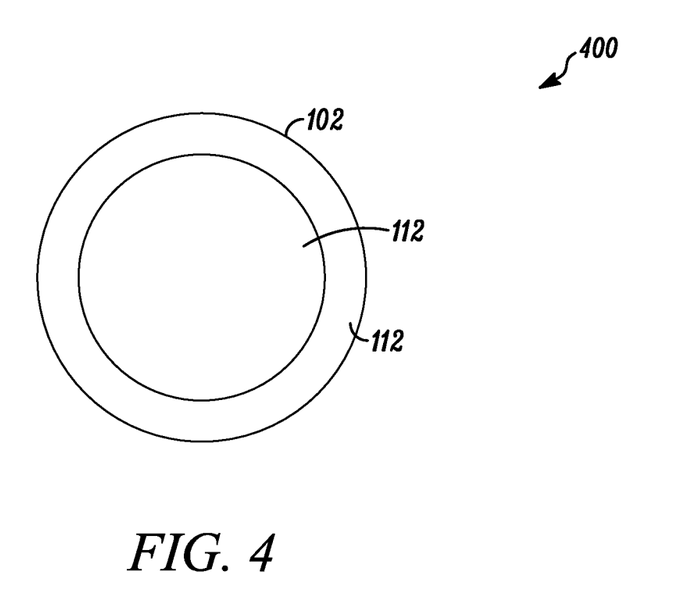
FIG. 4 is a front view of an articulating socket, according to some embodiments.

The articulating socket 102 may include an optional liner or lining 112 that substantially covers the front and inner surfaces of the articulating socket 102 (see front view 400 of FIG. 4). The lining 112 may be polyethylene or a metal or ceramic liner, for example. The lining 112 may be removeably attached to the articulating socket 102 or permanently or semi-permanently attached, for example. The lining 112 may be removable by utilizing a compression fit, locking tabs, friction or other mechanisms. The lining 112 may be permanently or semi-permanently attached by utilizing an adhesive or other bonding mechanism.

Figure 6:
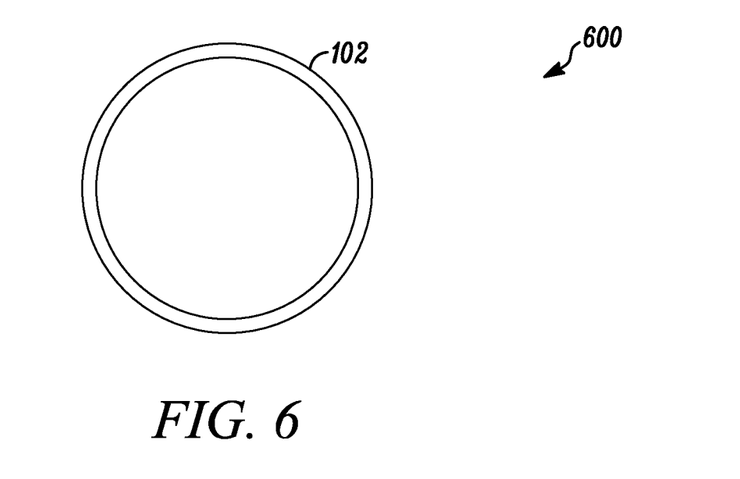
FIG. 6 is a front view of an articulating socket without liner, according to some embodiments.

The articulating socket 102 may be substantially hemispheric and may be manufactured of a durable material, suitable for invasive medical insertion, such as titanium, metal alloys or cobalt chromate, as examples. Alternatively, the articulating socket 102 can be polished metal or plastic and not utilize a separate lining 112 (see front view 600 of FIG. 6).

Figure 5:
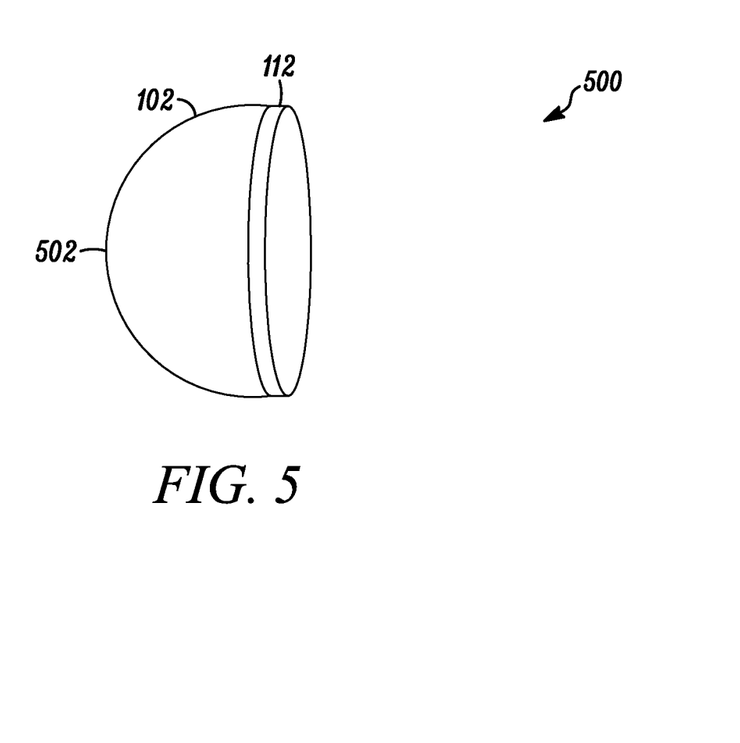
FIG. 5 is a side view of an articulating socket with liner, according to some embodiments.

The articulating socket 102 may include a fitting 502 for interaction with a stem component 106 (see side view 500 of FIG. 5). The fitting 502 may be male or female and may be separately attached or formed as a one-piece construction as part of the articulating socket 102. It may be desirable in revision surgery to utilize a female fitting 502 on the articulating socket 102. In such a procedure, once the existing ball is removed from the existing stem component, the female fitting 502 may be adapted to the male end of the stem, without removing it from the patient's bone. Examples of fittings 502 may be trunnions, such as morse taper trunnions. The fitting 502 may be centered on the distal or apex end of the articulating socket 102 or off set. The fitting 502 may be off set from the centerline of the socket 102 about 5 to about 20 degrees, about 10 to about 15 degrees or about 8 to about 12 degrees to allow for various configurations and positioning within the body.

The articulating socket 102 front surface (see view 400 of FIG. 4) may be planar or curved, for example. The front surface may be curved so as to lessen the possibility of unwanted interactions with other components of the device. Additionally, the socket opening may be 180 degrees planar when viewed from a side profile (see view 500 of FIG. 5) or alternatively, some angle less than 180 degrees. The articulating socket 102 opening may be about 150 to about 180 degrees, about 160 to about 170 degrees or about 165 to about 175 degrees, for example.

Figure 3:
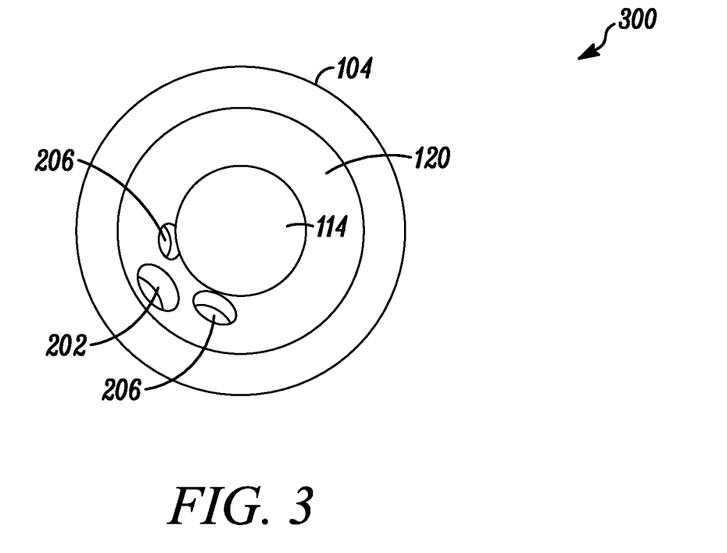
FIG. 3 is a front view of a fixed socket, according to some embodiments.
Figure 7:
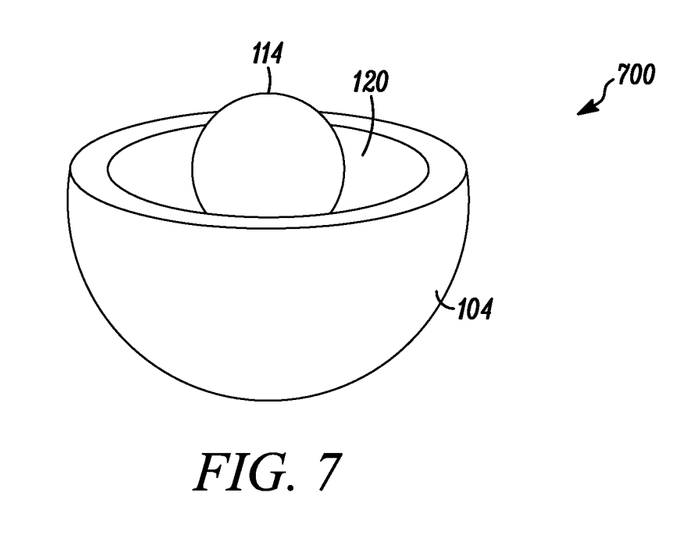
FIG. 7 is a perspective view of a fixed socket with ball, according to some embodiments.
Figure 8:
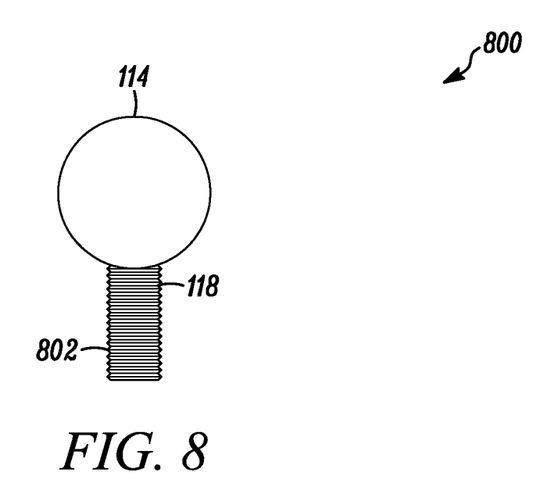
FIG. 8 is a perspective view of a ball and post, according to some embodiments.
Figure 9:
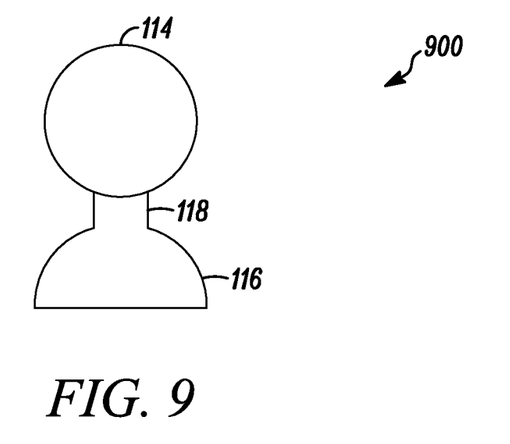
FIG. 9 is a perspective view of a ball and post with base, according to some embodiments.
Figure 10:
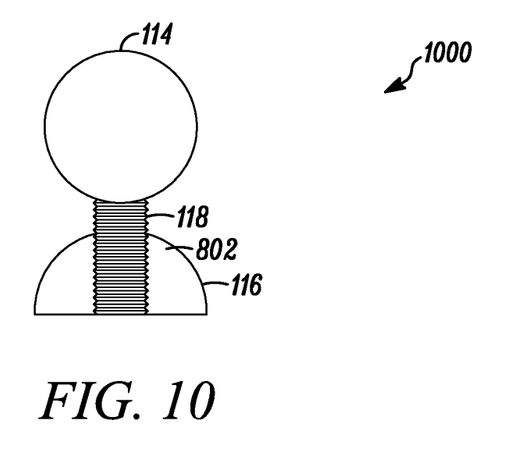
FIG. 10 is a perspective view of a ball and post with base, according to some embodiments.

The ball 114 is supported in a substantially center position within the fixed socket 104 (see front view 300 of FIG. 3 and perspective view 700 of FIG. 7). The center position may include attachment at the deepest portion of the socket 104, but also centered in height between the base and opening of the socket 104. The ball 114 can be supported by a post 118, such as a threaded post 802 (see view 800 of FIG. 8). The ball 114 can be supported by a post 118 with a flared base 116 or pedestal that resists or prevents substantial cantilever forces (see view 900 of FIG. 9). The ball 114 may be one-piece construction with the post 118 and optional base 116, for example. The post 118 may be threaded 802 without a base 116 or with a flared base 116, such as shown in view 1000 of FIG. 10. The post 118 may be of one-piece construction with the base 116, for example.

Figure 11:
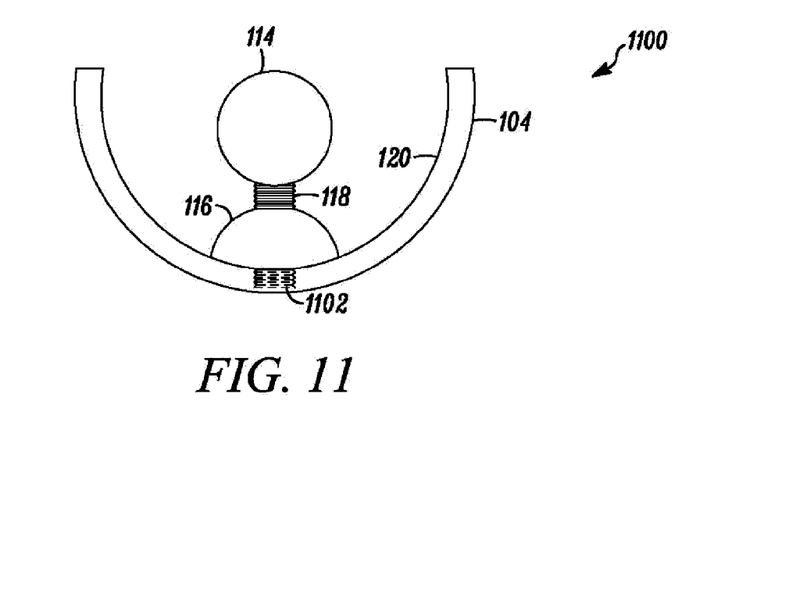
FIG. 11 is a cross-sectional view of a fixed socket with ball, according to some embodiments.

The ball 114 may be contacted and supported by the fixed socket 104 through an insertion tool fitting 1102 (and optionally 202 of FIG. 2), such as a screw hole (see cross-sectional view 1100 of FIG. 11). The insertion tool fitting screw hole 1102 may not extend through the entire fixed socket wall, for example. A physician may utilize the screw hole when inserting the original socket and in subsequent revision surgery as described herein, can use the existing insertion tool fitting hole to secure a new ball 114, via a post 118 or one-piece ball and post construction. The base 116 may match the curvature of the fixed socket 104 and be secured using locking tabs or other mechanical fastening mechanism or an adhesive, for example. Screw holes 206 (see FIG. 2) are often available in fixed socket construction for securing the socket 104 to bone, if needed. The base 116 may abut or partially cover these holes 206 and be secured by deforming soft metal tabs positioned in the screw holes 206, sufficient to disallow unintentional unscrewing of the post 118 or base 116 from the socket 104. The base 116 may be optionally secured using a torque wrench (if threaded and in contact with a screw hole, for example), manually screwed, secured by soft or deformable tabs or adhered with adhesive or cement, as examples. The size of the base 116 and surface area of the base may be as large as possible to increase support, but without being so large as to inhibit any desired articulation of the articulation socket 102 within the fixed socket 104. The base 116 may function as a stop for screw threading as well.

The fixed socket 104 may be substantially hemispheric and constructed of a durable material, suitable for invasive medical insertion, such as titanium, metal alloys or cobalt chromate.

Similarly to the articulating socket 102, the fixed socket 104 front surface (see view 300 of FIG. 3) may be planar or curved, for example. The front surface may be curved so as to lessen the possibility of unwanted interactions or impingements with other components of the device. Additionally, the socket opening may be 180 degrees planar when viewed from a side profile or alternatively, some angle less than 180 degrees. The fixed socket 104 opening may be about 150 to about 180 degrees, about 160 to about 170 degrees or about 165 to about 175 degrees, for example.

Figure 12:
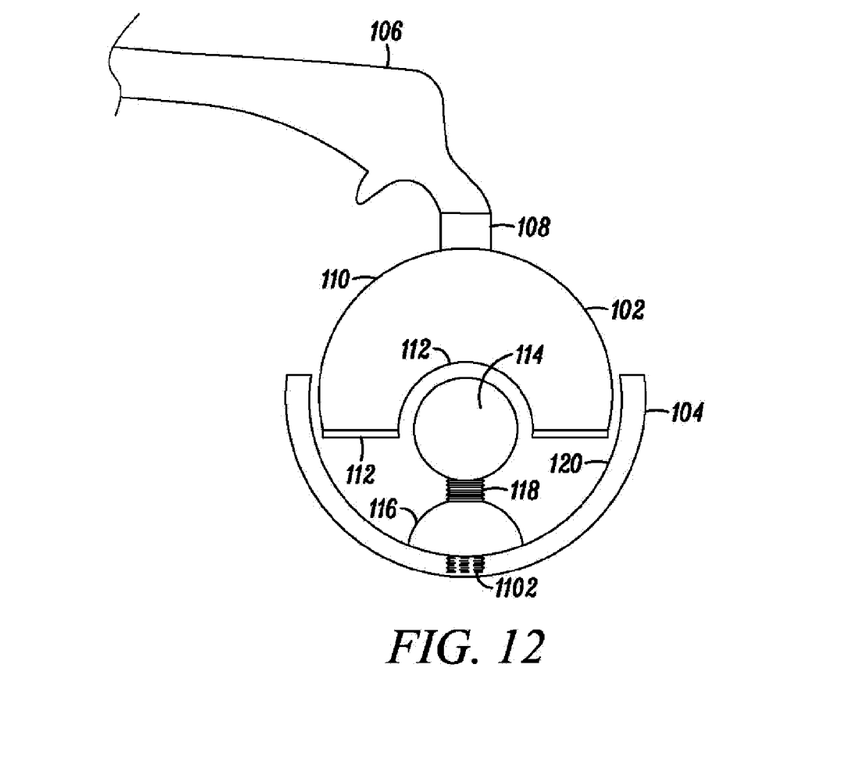
FIG. 12 is a cross-sectional view of a reverse joint replacement device, according to some embodiments.

Referring to FIG. 12, a cross-sectional view 1200 of a reverse joint replacement device is shown, according to some embodiments. The articulating socket 102 with optional lining 112 articulates with ball 114. If a dislocation begins, the outer surface of 102 will then come into contact with inner surface 120 of fixed socket 104, thus preventing the dislocation and supporting the force. An optional lining may be positioned around the periphery of the inner surface 120 of the fixed socket, such that when the outer surface of articulating socket 102 (which may be polished) contacts the fixed socket 104, stable articulation surfaces are utilized.

Figure 13:
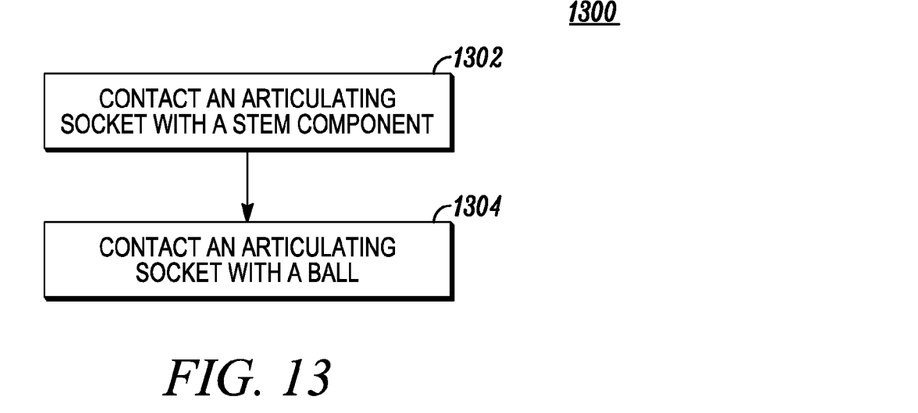
FIG. 13 is a block flow diagram of a method of using a joint replacement device, according to some embodiments.

Referring to FIG. 13, a block flow diagram 1300 of a method of using a joint replacement device is shown, according to some embodiments. An articulating socket is contacted 1302 with a stem component. The articulating socket is then contacted 1304 with a ball supported by a fixed socket. In a revision surgery, an articulating socket may replace an existing ball on a stem component, such as a femoral stem component. A ball may be positioned in the fixed socket. Once again, if in a revision surgery, a ball may be attached to an existing fixed socket without removing it. The stem component may include a male or female fitting and the articulating socket may be matched or adapted to interact with a new or existing stem component.

In a primary surgery, there are more options for utilizing one-piece construction. The fixed socket and ball (with post and optional base) may be made of one-piece construction and inserted as a single unit. Similarly, the articulating socket may be formed of one-piece construction with the stem component. The stem component and articulating socket may then be inserted as a single unit. The ball may be of a differing material than base or stem to maximize the articulation between ball and articulation socket.

Figure 14:
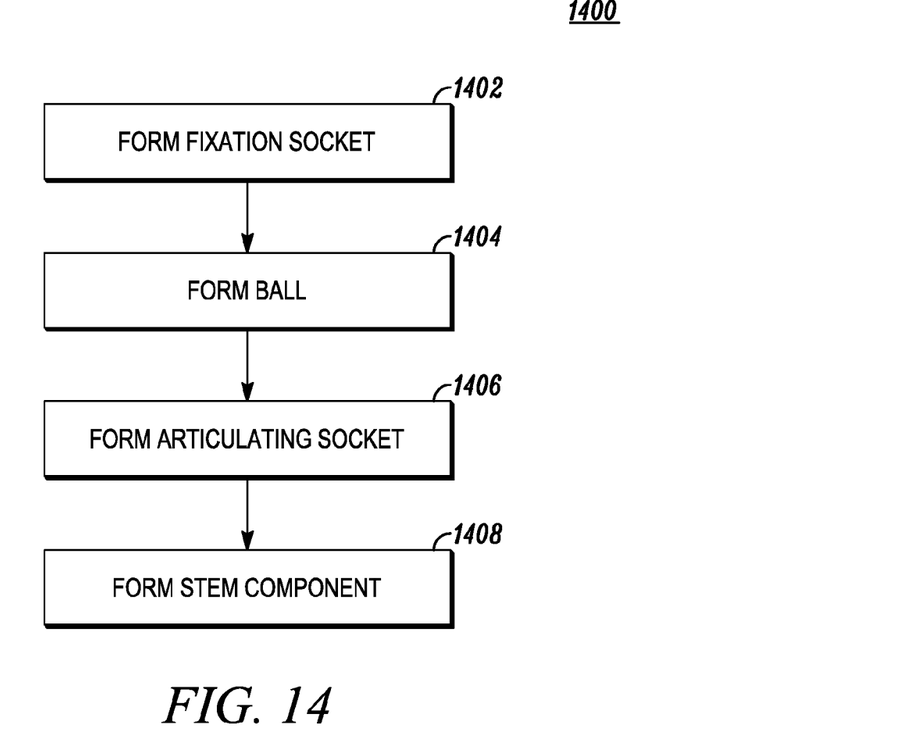
FIG. 14 is a block flow diagram of a method of making a joint replacement device, according to some embodiments.

Referring to FIG. 14, a block flow diagram 1400 of a method of making a joint replacement device is shown, according to some embodiments. A fixed socket is formed 1402, including an inner surface and outer surface. A ball is formed 1404, supported by the inner surface of the fixed socket. The ball may be one-piece construction with the fixed socket, for example. Alternatively, it can be formed separately and attached to the fixed socket. An articulating socket is formed 1406 and a stem component is formed 1408. The articulating socket may be of one-piece construction with the stem component for example. Alternatively, the articulating socket may be formed separately and attached to the stem component.

The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims.

What is claimed is:

1. A reverse joint replacement device, comprising:
    a fixed socket, including an inner surface and a socket insertion tool fitting;
    a post removably attached to the socket insertion tool fitting
    a ball removably attached to the post;
    an articulating socket including an inner surface and an outer surface, the inner surface in contact with the ball; and
    a stem component, attached to the outer surface of the articulating socket;
    wherein the inner surface of the articulating socket articulates with the ball and the outer surface of the articulating socket can articulate with the inner surface of the fixed socket.

2. The reverse joint replacement device of claim 1, further comprising the stem component adapted to contact with a bone of a patient.

3. The reverse joint replacement device of claim 1, further comprising the outer surface of the fixed socket adapted to contact with an acetabulum or glenoid fossa of a patient.

4. The reverse joint replacement device of claim 1, wherein the inner surface of the articulating socket comprises a liner.

5. The reverse joint replacement device of claim 1, wherein attaching comprises screwing, gluing or forming.

6. The reverse joint replacement device of claim 1, wherein the post includes a flared base for resisting cantilever forces.

7. The reverse joint replacement device of claim 1, wherein the stem component comprises a femoral stem component.

8. The reverse joint replacement device of claim 1, wherein the stem component is attached to the outer surface of the articulating socket by an adjustable fitting.

9. The reverse joint replacement device of claim 8, wherein the fitting is positioned on the centerline of the articulating socket.

10. The reverse joint replacement device of claim 8, wherein the fitting is off set from the centerline of the socket by about 5 degrees to about 20 degrees.

11. The reverse joint replacement device of claim 1, wherein the ball and post are a one-piece construction.

12. The reverse joint replacement socket of claim 11, wherein the flared base at least partially covers the screw holes.

13. A reverse joint replacement socket, comprising:
    a substantially hemispherical concave socket;
    a substantially flared base for resisting cantilever forces removably attached to the socket at an insertion tool fitting; and
    a ball, adjustably attached to a post of the flared base;
    wherein the socket can attach to an acetabulum or glenoid fossa.

14. The reverse joint replacement socket of claim 13, further comprising screw holes.

15. The reverse joint replacement socket of claim 14, wherein the flared base is held in place by tabs positioned in the screw holes.

16. The reverse joint replacement socket of claim 13, wherein the socket comprises an opening of about 150 degrees to about 180 degrees.

17. The reverse joint replacement socket of claim 13, wherein the ball is attached in a substantially centered position at the deepest portion of the socket.

18. The reverse joint replacement socket of claim 13, wherein the ball is attached in a substantially centered position and centered in height between the base and opening of the socket.

19. The reverse joint replacement socket of claim 13, wherein the base matches the curvature of the socket.

* * * * *